United States Patent
De Rugeriis et al.

(10) Patent No.: US 9,655,978 B2
(45) Date of Patent: May 23, 2017

(54) METHOD FOR PREPARING NANOHYDROGEL

(71) Applicant: NIOB SAGL, Lugano (CH)

(72) Inventors: Maria Cristina De Rugeriis, Avezzano (IT); Elita Montanari, Castel Madama (IT); Chiara Di Meo, Bucchianico (IT); Pietro Matricardi, Rome (IT)

(73) Assignee: NIOB Sagl, Lugano (CH)

( * ) Notice: Subject to any disclaimer, the term of this patent is extended or adjusted under 35 U.S.C. 154(b) by 0 days.

(21) Appl. No.: 14/896,847

(22) PCT Filed: Jun. 11, 2014

(86) PCT No.: PCT/IB2014/062138
§ 371 (c)(1),
(2) Date: Dec. 8, 2015

(87) PCT Pub. No.: WO2014/199318
PCT Pub. Date: Dec. 18, 2014

(65) Prior Publication Data
US 2016/0121000 A1 May 5, 2016

(30) Foreign Application Priority Data
Jun. 11, 2013 (IT) .............................. RM2013A0339

(51) Int. Cl.
| | | |
|---|---|---|
| C08J 3/075 | (2006.01) |
| A61K 47/48 | (2006.01) |
| A61K 47/36 | (2006.01) |
| A61K 9/06 | (2006.01) |
| A61K 9/107 | (2006.01) |
| A61K 31/5383 | (2006.01) |

(52) U.S. Cl.
CPC .......... *A61K 47/48784* (2013.01); *A61K 9/06* (2013.01); *A61K 9/1075* (2013.01); *A61K 31/5383* (2013.01); *A61K 47/36* (2013.01); *A61K 47/4823* (2013.01); *A61K 47/48123* (2013.01); *A61K 47/48869* (2013.01); *C08J 3/075* (2013.01); *C08G 2210/00* (2013.01); *C08J 2305/00* (2013.01); *C08J 2305/08* (2013.01)

(58) Field of Classification Search
CPC ................................. C08J 3/075; A61K 47/36
See application file for complete search history.

(56) References Cited

FOREIGN PATENT DOCUMENTS

| | | |
|---|---|---|
| EP | 1 666 075 | 6/2006 |
| JP | 2007/068696 | 3/2007 |

OTHER PUBLICATIONS

I. Lee, et al. "Single molecular mechanics of a cholesterol-bearing pullulan nanogel at the hydrophobic interfaces", Biomaterials, Elsevier Science Publishers BV., Barking, GB, vol. 25, No. 15, Jul. 1, 2004, pp. 2911-2918.

G. D' Arrigo, et al. "Self-assembled gellan-based nonohydrogels as a tool for prednisolone delivery", Soft Matter, vol. 8 No. 45, Jan. 1, 2012, pp. 11557-11564.

K. Akiyoshi, et al. "Microscopic Structure and Thermoresponsiveness of a Hydrogel Nanoparticle by Self-Assembly of a Hydrophobized Polysaccharide", Macromolecules, American Chemical Society, US, vol. 30, No. 4, Jan. 1, 1997, pp. 857-861.

*Primary Examiner* — Carlos Azpuru
(74) *Attorney, Agent, or Firm* — Blank Rome LLP

(57) ABSTRACT

A method for preparing nanohydrogels comprising a dispersion step, in which a polysaccharide functionalized with hydrophobic molecules and in the form of a macromolecular agglomerate is dispersed in an aqueous solution, and a heating step, in which the aqueous dispersion of the polysaccharide is subjected to a temperature of between 70° C. and 150° C. and a pressure of between 1 bar and 5 bar. In the heating step, the conditions of temperature and pressure must be such that boiling of the aqueous dispersion of the polysaccharide does not take place.

8 Claims, No Drawings

METHOD FOR PREPARING NANOHYDROGEL

TECHNICAL FIELD

The present invention relates to a method for preparing highly sterile nanohydrogels.

By the term "nanohydrogels" is meant a particular type of nanoparticles with a size of between 10 nm and 1000 nm that is able to combine the advantages of hydrogels with those of nanotechnology, such as for example high flexibility, versatility, water absorption, high biocompatibility and long stay times within the organism.

BACKGROUND ART

In general, it is known that a polysaccharide (of a hydrophilic nature) appropriately functionalized with molecules of a hydrophobic nature can provide an assembling system with nanohydrogel characteristics if exposed to particular conditions in an aqueous environment.

Nanohydrogels are acquiring a certain importance in the pharmaceutical field since, if they are rendered sterile and apyrogenic, they can be used as compounds vehicling the drugs and be administered both in humans and in animals via inhalatory or parenteral route (i.v., i.m., s.c.,) or else topically, with the aid of an appropriate device.

There are currently known various methods for preparing nanohydrogels starting from functionalized polysaccharides.

A first of these methods consists in subjecting the functionalized polysaccharide to sonication. Ultrasonic vibrations are able to induce formation of nanohydrogels of small dimensions. Ultrasounds generate in the polymeric suspension micro-bubbles that by imploding give rise to the phenomenon of cavitation, which promotes separation of the polymeric chains, thus favouring formation of a nanoparticle suspension. This technique, however, presents numerous disadvantages at an industrial level such as high polydispersion of the specimen, high costs, and an enormous production of heat.

Another method consists in solubilizing the functionalized polysaccharide in an appropriate solvent and adding drop by drop the solution obtained in water. In these conditions, the system precipitates, inducing formation of nanoparticles. This method of preparation presents disadvantages as regards the particularly high costs, complex manual operations that are hard to reproduce, and very long preparation times.

Furthermore, this methodology envisages the use of organic solvents, with obvious disadvantages in terms of toxicity and safety that these represent.

Yet another method consists in subjecting to dialysis against water or aqueous solution the functionalized polysaccharide once this has been solubilized in an organic solvent. The slow entry of water through the dialysis tubes causes formation of nanohydrogels of small dimensions by spontaneous self-assembly. The disadvantages that this method involves regard the presence of aggregates in a more or less significant amount, lack of reproducibility, particularly high costs, and particularly long preparation times. Furthermore, also in this case the presence of organic solvents raises problems of safety and toxicity.

As mentioned above, one of the possible applications of nanohydrogels is the one regarding pharmaceutical preparations administered via parenteral route. Nanohydrogels, in fact, can englobe a pharmacologically active principle and function as carrier for its administration.

In this context, a treatment of sterilization of the nanohydrogels becomes indispensable. The methods of sterilization used by pharmaceutical industries are not, however, totally satisfactory.

One of the main sterilization methods used is filtration by means of filters with a porosity equal to or less than 0.22 µm, following the pharmacopoeia recommendations. Even though filtration is possible, as a rule, with systems of suitable dimensions, it is in any case frequently problematical on account of clogging of the filters themselves due to the interactions that may arise between the nanoparticles and the materials constituting the filters. Furthermore, it has been found that filtration may cause, as a mechanical effect, destructuring of the nanoparticles, for example vesicles such as liposomes, causing loss from the medicament of the bio-active molecules, which remain trapped on the filter, and/or their leakage into the transport liquids.

Another sterilization method consists in irradiation with gamma rays or with a electron flow. This procedure presents the disadvantage of being able to alter the structure of the fragile bio-active molecules, cause a degradation of the polymers that constitute the pharmaceutical form, and alter the integrity of the phospholipids constituting the liposomes.

Another method used for sterilization moreover envisages the use of gases, such as ethylene oxide; this technique, however, is not easy to implement in the presence of substances that can react with the gas itself. Furthermore, also the intimate contact with the pharmaceutical forms, which is necessary to achieve sterility, may be problematical, as likewise removal of the gas prior to packaging of the pharmaceutical form itself.

There is hence felt the need to provide a methodology that will be able to prepare nanohydrogels and to sterilize them without incurring in the drawbacks of the known art.

An extremely simple and economically advantageous method for preparing directly sterile nanohydrogels with a high dimensional homogeneity has been unexpectedly found by the inventors of the present patent application.

DISCLOSURE OF INVENTION

The subject of the present invention is a method for preparing nanohydrogels, characterized in that it comprises a dispersion step, in which a polysaccharide functionalized with hydrophobic molecules is dispersed in an aqueous solution to obtain an aqueous dispersion of polysaccharide, and a heating step, in which the aqueous dispersion of the polysaccharide is subjected to a temperature of between 70° C. and 150° C. and a pressure of between 1 bar and 5 bar; in this heating step, the conditions of temperature and pressure must be such that boiling of the aqueous dispersion of the polysaccharide does not take place.

BEST MODE FOR CARRYING OUT THE INVENTION

Preferably, the heating step envisages a temperature of between 90° C. and 130° C. and a pressure of between 1.5 bar and 3.5 bar.

Preferably, the heating step has a duration of between 5 min and 3 hours.

Preferably, in the dispersion step the polysaccharide functionalized with hydrophobic molecules is dispersed in an aqueous solution at a concentration of between 0.1 mg/ml and 10.0 mg/ml.

Preferably, the aqueous dispersion of the polysaccharide comprises one or more compounds designed to be englobed and/or adsorbed in the nanohydrogel particles formed in the subsequent heating step.

Preferably, the aforesaid compound designed to be englobed and/or adsorbed in the nanohydrogel particles is a cryoprotective compound and/or a pharmacologically active compound.

Preferably, said cryoprotective compound is added to the aqueous solution of the polysaccharide in a concentration of between 0.10% w/v and 20.0% w/v.

Preferably, said cryoprotective compound is comprised in the group made up of dextrose, maltose, trehalose, lactose, and saccharose.

Preferably, said pharmacologically active compound is added to the aqueous dispersion of the polysaccharide in a concentration of between 0.05 mg/ml and 10.0 mg/ml.

Preferably, nanohydrogels are self-assembled nanohydrogels derived from polysaccharides functionalized with molecules having a hydrophobic nature.

Preferably, the polysaccharide is comprised in the group constituted by hyaluronic acid, pullulan, dextran, gellan gum, scleroglucan, chitosan, alginate, guaran, xanthan gum, chitosan, and cyclodextrin.

Preferably, said pharmacologically active compound is comprised in the group made up of antibiotics, anti-cancer agents, analgesics, anti-inflammatory agents, anaesthetics, analeptics, adrenergic agents, adrenergic blocking agents, anticholinergic agents, anticolinesterasic agents, anticonvulsivants, adrenocorticotropic agents, adrenolytic agents, adrenomimetic agents, alkylating agents, alkaloids, allosteric inhibitors, anabolic steroids, anorectics, antacids, antidotes, antidiarrhoeal agents, antifolates, antipyretics, antirheumatic agents, psychotherapeutic agents, neural blocking agents, antiemetics, anthelmintics, antiarrhythmic agents, antitubercular agents, anticoagulants, antidepressants, antidiabetic agents, antiepileptic agents, antifungal agents, histamine antagonists, antihypertensives, muscarinic antagonists, antimycobacterials, antimalarial agents, antiseptics, antiprotozoal agents, immunosuppressants, immunostimulants, antithyroid agents, antiviral agents, anxiolytics, sedatives, astringents, beta-blocking agents, contrast media, corticosteroids, anticough agents, diagnostic agents, image-diagnostic agents, diuretics, dopaminergic agents, haemostatic agents, haematological agents, haemoglobin modifiers, hormones, hypnotic agents, hypolipidemizing agents, lipid-regulating agents, muscarinic agents, parasympathicomimetic agents, myorelaxing agents, prostaglandins, sedatives, sexual hormones, anti-allergens, stimulating agents, sympathicomimetic agents, thyroid agents, vasodilators, vaccines, vitamins, xanthines, anti-neoplastic agents, proteins, polypeptides, carbohydrates, polynucleotides, nucleic acids, and polyclonal or monoclonal antibodies.

EXAMPLES

For a better understanding of the invention, provided hereinafter are examples of embodiment having an explanatory and non-limiting purpose.

In the ensuing examples the size of the nanohydrogel particles was measured using the DLS (Dynamic Light Scattering) technique (Submicron Particle Sizer Autodilute Model 370, Nicomp).

Example 1: Formation of Gellan Gum-Cholesterol (Ge-CH) Nanohydrogels

The gellan gum was appropriately functionalized with a hydrophobic cholesterol unit so as to obtain a (gellan gum-cholesterol, Ge-CH) stable beyond in the form of a macromolecular agglomerate. An amount of 3 mg of (Ge-CH) amphiphilic polymer was dispersed in 3 ml of water and left under plate stirring for 12 hours. The dispersion deriving from the aqueous solution was introduced into a glass container, which was then closed and put into an autoclave for sterilization. In the autoclave the dispersion was subjected for 20 minutes to a temperature of 121° C. and a pressure of 2 bar. At the end of the treatment, Ge-CH nanohydrogels were obtained having a size of 200±5 nm, and with a polydispersion index of 0.200±0.05.

The dimensional stability of Ge-CH nanohydrogels was studied at 37° C. for 15 days so as to mimic the physiological conditions, and at 4° C. for 15 days so as to mimic the conditions of preservation of the product in a refrigerator. The Ge-CH nanohydrogels formed at high temperature and high pressure proved stable at high and low preservation temperatures.

Furthermore, the potential ζ of the Ge-CH nanohydrogels was measured using the DLS technique, and the value obtained was 20±5.0 mV and remained stable for over 48 hours.

Example 2: Formation of Hyaluronic Acid-Cholesterol (HA-CH) Nanohydrogels

The hyaluronic acid was appropriately functionalized with a hydrophobic cholesterol unit so as to obtain a (hyaluronic acid-cholesterol, HA-CH) amphiphilic polymer in the form of a macromolecular agglomerate. An amount of 5 mg of the (HA-CH) amphiphilic polymer was dispersed in 3 ml of water and left under plate stirring for 12 hours. The dispersion obtained was introduced into an appropriate glass container, which was then closed and put into an autoclave. In the autoclave, the dispersion was subjected for 30 minutes to a temperature of 90° C. and a pressure of 1.5 bar.

At the end of the treatment, HA-CH nanohydrogels were obtained having a size of 380±20 nm, and with a polydispersion index of 0.325±0.077.

The stability of HA-CH nanohydrogels was studied at 4° C. for 7 days so as to mimic the conditions of preservation of the product in a refrigerator. The HA-CH nanohydrogels formed at high temperature and high pressure proved stable at low preservation temperatures for over 7 days.

Example 3: Formation of Gellan Gum-Polylactic Acid (Ge-PLA) Nanohydrogels

The gellan gum was appropriately functionalized with a hydrophobic polylactic-acid unit so as to obtain a (gellan gum-polylactic acid, Ge-PLA) amphiphilic polymer in the form of a macromolecular agglomerate. An amount of 7 mg of the (Ge-PLA) amphiphilic polymer was dispersed in 3 ml of water and left under plate stirring for 12 hours. The dispersion obtained was introduced into a glass container, which was then closed and put into an autoclave. In the autoclave, the dispersion was subjected for 15 minutes to a temperature of 130° C. and a pressure of 2.5 bar.

At the end of the treatment, Ge-PLA nanohydrogels were obtained having a size of 180±20 nm, and with a polydispersion index of 0.325±0.095.

Example 4: Formation and Lyophilization of Hyaluronic Acid-Cholesterol (HA-CH) Nanohydrogels The (HA-CH) amphiphilic polymer in the form of macromolecular agglomerate was dispersed in an aqueous solution (3 mg/ml) comprising dextrose as cryoprotectant at the concentration of 1% w/v and left under plate stirring at room temperature for 12 hours. The dispersion thus obtained was introduced into an appropriate glass container, which was then closed and put into an autoclave. In the autoclave, the dispersion was subjected for 20 minutes to a temperature of 121° C. and a pressure of 2 bar.

At the end of the treatment HA-CH nanohydrogels were obtained having a size of 380±20 nm.

The nanohydrogels thus obtained can be subjected directly to lyophilization according to the known art so as to obtain a lyophilizate, which is convenient to transport and handle and is stable over long periods of time. The lyophilizate obtained was re-suspended with sterile water or with physiological solutions also after 6 months from preparation, and it was always possible to re-obtain the HA-CH nanohydrogels with a size of 400±10.

Example 5: Formation and Charging of Gellan Gum-Cholesterol (Ge-CH) Nanohydrogels with the Antibiotic Levofloxacin The (Ge-CH) amphiphilic polymer in the form of macromolecular agglomerate was dispersed in aqueous solution (1 ml, 2 mg/ml) and left under plate stirring at room temperature for 12 hours. The dispersion was then added with 1 ml of a 0.66-mg/ml solution of a fluoroquinolone antibiotic (levofloxacin) thus obtaining a final concentration of antibiotic of 0.33 mg/ml. The mixture thus obtained was introduced into an appropriate glass container, which was then closed and put into an autoclave. In the autoclave, the dispersion was subjected for 20 minutes to a temperature of 121° C. and a pressure of 2 bar. At the end of the process, the dispersion was subjected to dialysis (Visking tubing, cut-off: 12000-14000) for 3 hours against distilled water so as to purify the nanohydrogels from the drug not encapsulated therein. After dialysis, Ge-CH nanohydrogels charged with levofloxacin were obtained having a size of 230±3.0 nm, and with a polydispersion index of 0.20±0.03.

In order to assess the trapping efficacy of the drug in the Ge-CH nanohydrogels, these were lyophilized and solubilized in N-methyl-pyrrolidone so as to break the nanohydrogels and free the levofloxacin trapped therein. The trapping efficacy (percent encapsulation) was determined from the ratio of the amount of levofloxacin encapsulated in the nanohydrogels to the total amount of nanohydrogels produced. The concentration of levofloxacin in solution was measured using a UV-VIS spectrophotometer at the wavelength of absorbance of levofloxacin of 302 nm, using a calibration straight line that was obtained in a concentration range of between 0.75 and 12.0 µg/ml.

The trapping efficacy of levofloxacin in the Ge-CH nanohydrogels was 5% with respect to the weight of the polymer.

The same identical results were obtained using HA-CH nanohydrogels.

Example 6: Formation, Charging, and Lyophilization of Hyaluronic Acid-Cholesterol (HA-CH) Nanohydrogels with the Antibiotic Levofloxacin The (HA-CH) amphiphilic polymer in the form of macromolecular agglomerate was dispersed in an aqueous solution (3 mg/ml) comprising dextrose as cryoprotectant at the concentration of 1% w/v and left under plate stirring at room temperature for 12 hours. The dispersion was added with 1 ml of a solution of a fluoroquinolone antibiotic (levofloxacin) to obtain a final concentration of antibiotic of 1 mg/ml. The mixture thus obtained was introduced into an appropriate glass container, which was then closed and put into an autoclave. In the autoclave, the dispersion was subjected for 20 minutes to a temperature of 121° C. and a pressure of 2 bar.

At the end of the process, the dispersion was subjected to sterile diafiltration so as to purify the nanohydrogels from the drug not encapsulated therein. After filtration, HA-CH nanohydrogels charged with levofloxacin and sterile were obtained, having a size of 380±20 nm, and with a polydispersion index of 0.325±0.07.

The nanohydrogels produced were lyophilized according to the known art, and then the lyophilizate was re-suspended in an amount of sterile water such as to obtain a concentration of charged nanohydrogels of 1 mg/ml. The dispersion was sized using the DLS technique, and from the results it emerged that, in these conditions, the nanohydrogels maintain roughly the same starting size (384±7 nm).

In order to assess the trapping efficacy of the drug in the HA-CH nanohydrogels, these were lyophilized and solubilized in N-methyl-pyrrolidone so as to break the nanohydrogels and free the levofloxacin trapped therein. The trapping efficacy (percent encapsulation) was determined by the ratio of the amount of levofloxacin encapsulated in the nanohydrogels to the amount of nanohydrogels. The concentration of levofloxacin in solution was measured using a UV-VIS spectrophotometer at the wavelength of absorbance of levofloxacin of 302 nm, using a calibration straight line that was obtained in a range of concentrations of between 0.75 µg/ml and 12.0 µg/ml.

The trapping efficacy of levofloxacin in HA-CH nanohydrogels was 5% with respect the weight of the polymer.

From the description of the examples referred to above, it is evident how the method according to the present invention presents the major advantage of enabling preparation in an extremely simple and economically advantageous way of nanohydrogels that are directly sterile and present a high dimensional homogeneity.

The nanohydrogels that form the subject of the present invention derive from an amphiphilic polysaccharide matrix which, if subjected to high pressure and high temperature, is able to form nanohydrogels by self-assembly. These nanohydrogels can simultaneously encapsulate or adsorb a large number of active principles, which are protected by the polymeric system during the sterilization process.

It should be pointed out how the method forming the subject of the present invention enables preparation of nanohydrogels that are directly sterile and apyrogenic and induces drug/polymer assembly without causing degradation of the pharmacologically active compound or degradation of the polymer.

The method forming the subject of the present invention presents the major advantage of enabling preparation of nanohydrogels that, in addition to being sterile and apyrogenic, can be charged both with a drug and with a cryoprotective compound. This means that the sterile and apyrogenic nanohydrogels that vehicle the drug can be subjected to a process of lyophilization so as to be preserved in the form of lyophilizate that remains stable over long periods and is convenient to handle and transport. Lyophilised nanohydrogels can be reconstituted in water or in adequate solutions, such as, for example, physiological solutions, perserving the same initial characteristics.

The lyophilization process can be carried out in the same autoclave as the one used for preparation.

Finally, it should be emphasized how the method according to the present invention is not aimed exclusively at applications of a biomedical and/or pharmaceutical nature, but can be employed effectively in all those applications that require the use of polysaccharidic nanohydrogels.

The invention claimed is:

1. A method for preparing nanohydrogels, characterized in that it comprises a dispersion step, in which a polysaccharide functionalized with hydrophobic molecules is dispersed in an aqueous solution to obtain an aqueous dispersion of the polysaccharide, and a heating step, in which the aqueous dispersion of the polysaccharide is subjected to a temperature of between 70 and 150° C. and a pressure of between 1 and 5 bar; in said heating step the conditions of temperature and pressure must be such that boiling of the aqueous dispersion of the polysaccharide does not take place.

2. The method for preparing nanohydrogels according to claim 1, characterized in that the heating step envisages a temperature of between 90° C. and 130° C. and a pressure of between 1.5 bar and 3.5 bar.

3. The method for preparing nanohydrogels according to claim 1, characterized in that the heating step has a duration of between 5 min and 3 h.

4. The method for preparing nanohydrogels according to claim 1, characterized in that in the dispersion step the polysaccharide functionalized with hydrophobic molecules is dispersed in an aqueous solution at a concentration of between 0.1 mg/ml and 10.0 mg/ml.

5. The method for preparing nanohydrogels according to claim 1, characterized in that the aqueous dispersion of the polysaccharide comprises a compound designed to be englobed and/or adsorbed in the nanohydrogel particles formed in the subsequent heating step.

6. The method for preparing nanohydrogels according to claim 5, characterized in that the aforesaid compound designed to be englobed and/or adsorbed in the nanohydrogel particles is a cryoprotective compound and/or a pharmacologically active compound.

7. The method for preparing nanohydrogels according to claim 6, characterized in that said cryoprotective compound is added to the aqueous dispersion of the polysaccharide in a concentration of between 0.10% w/v and 20.0% w/v.

8. The method for preparing nanohydrogels according to claim 5, characterized in that the aforesaid pharmacologically active compound is added to the aqueous dispersion of the polysaccharide in a concentration of between 0.05 mg/ml and 10.0 mg/ml.

* * * * *